US006921387B2

(12) United States Patent
Camrud

(10) Patent No.: US 6,921,387 B2
(45) Date of Patent: Jul. 26, 2005

(54) VASCULAR NEEDLE

(75) Inventor: Allan R. Camrud, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 0 days.

(21) Appl. No.: 10/137,985

(22) Filed: May 1, 2002

(65) Prior Publication Data

US 2002/0177864 A1 Nov. 28, 2002

Related U.S. Application Data

(60) Provisional application No. 60/287,956, filed on May 1, 2001.

(51) Int. Cl.[7] .......................... A61M 5/178; A61M 5/32

(52) U.S. Cl. .................................. 604/164.06; 604/274

(58) Field of Search ........................... 604/158, 164.01, 604/164.06, 187, 239, 264, 272, 273, 274

(56) References Cited

U.S. PATENT DOCUMENTS

| | | | | |
|---|---|---|---|---|
| 3,119,391 A | | 1/1964 | Harrison | |
| 4,585,446 A | | 4/1986 | Kempf | |
| 4,666,438 A | | 5/1987 | Raulerson | |
| 5,709,671 A | * | 1/1998 | Stephens et al. | 604/264 |
| 5,938,679 A | | 8/1999 | Freeman et al. | |

FOREIGN PATENT DOCUMENTS

| | | |
|---|---|---|
| DE | 42 26 476 | 8/1993 |

* cited by examiner

*Primary Examiner*—Nickolas D. Lucchesi
*Assistant Examiner*—Mark K. Han
(74) *Attorney, Agent, or Firm*—Merchant & Gould P.C.

(57) ABSTRACT

A hollow medical needle having a bevel face defining a needle tip and cutting surface that create a first incision. The needle additionally has a separate cutting blade extending outward from the needle. The blade is positioned adjacent the bevel face to create a second incision which intersects the first incision made by the bevel face cutting surface.

8 Claims, 6 Drawing Sheets

VASCULAR NEEDLE

CROSS REFERENCE TO RELATED APPLICATIONS

This application claims the benefit of the filing date of U.S. Provisional Application Ser. No. 60/287,956 entitled "VASCULAR NEEDLE", which was filed May 1, 2001.

FIELD OF THE INVENTION

The invention is directed to a hollow needle suitable for medical applications involving insertion of the needle into a blood vessel or other tissue, especially for the introduction or removal of fluids. More particularly, the invention provides a vascular needle adapted for use in medical procedures involving inserting a catheter into a vein or artery.

BACKGROUND OF THE INVENTION

Hollow needles are used for medical applications involving insertion of the needle into a blood vessel or other tissue, especially for the introduction or removal of fluids. Vascular needles are used in medical procedures involving inserting a catheter into a vein or artery. Catheter insertion may be achieved via percutaneous or surgical routes. Catheterization involves single-wall puncture of a vein or artery with a hollow needle, followed by insertion of a guidewire, withdrawal of the needle and insertion of a catheter over the guidewire.

In general, any hollow needle may be used for introducing a catheter into a vein or artery. However, hypodermic needles have long bevels designed for entering a blood vessel to withdraw blood, making them less suitable for inserting a catheter.

Vascular needles generally have thin walls to allow passage of a guidewire without increasing the outer diameter of the needle, and the corresponding size of the puncture hole. Vascular needles generally have a relatively short bevel at the tip with two cutting surfaces.

When a standard vascular needle is inserted into a vein or artery, the bevel cutting surfaces cause a substantially straight-line incision. This type of incision is shown in FIGS. 1–2, labeled "Prior Art". Using the numbers on a clock face for reference, the incision 10 in a vessel 12 is generally made between the 3 and 9 o'clock positions, as shown in FIG. 1, and must be wide enough to accommodate a cylindrical catheter.

Based on the geometry of inserting a cylindrical object into a straight-line incision, the incision 10 must be longer than the diameter of a cylindrical catheter 14, as shown in FIG. 2. If the incision 10 is too narrow, insertion of the catheter 14 may result in tearing of the vessel wall 12. An incision that is too long may cause excessive bleeding and require suturing after placement of the catheter.

Thus, a need remains for a vascular needle that creates an incision that reduces the risk of tearing when a catheter is inserted.

SUMMARY OF THE INVENTION

In its broadest terms, the invention is directed to a vascular needle that creates a double incision that reduces the risk of tearing, as well as to the use of that vascular needle. The invention is directed to a vascular needle that is configured to provide a lateral incision within an artery or vein, and is further configured to provide a relief incision.

In a preferred embodiment, the invention is found in a needle that includes a hollow cylindrical member that has a longitudinal axis and first and second ends. A bevel face is formed in a top surface of the first end of the cylindrical member, where the bevel face defines at least a first cutting surface, a needle tip, and a rear portion. The needle also includes at least a first projection that is attached to and extends away from the cylindrical member. The first projection defines at least a second cutting surface and is positioned proximal to the first end of the cylindrical member.

Another preferred embodiment of the present invention is found in a method for inserting a cylindrical component into a blood vessel. A lateral incision is made across the top of a vessel, at least one non-lateral relief incision is made adjacent to and connecting with the lateral incision, and the cylindrical component is inserted.

Another preferred embodiment is a needle that includes a first needle portion with a hollow cylindrical configuration having a longitudinal axis and first and second ends. The first need portion has a bevel face formed in a top surface of the first end that defines a first cutting surface, a needle tip, and a rear portion. The needle also includes a second needle portion with an elongate member having a longitudinal axis and first and second ends. The second needle portion has a cutting edge secured to the first end of the elongate member that defines a second cutting surface. The second needle portion is insertable into the first needle portion to position the second cutting surface adjacent the first end of the first needle portion.

BRIEF DESCRIPTION OF THE DRAWINGS

The invention may be more completely understood in consideration of the following detailed description of various embodiments of the invention in connection with the accompanying drawings, wherein like numerals represent like parts throughout several views, in which.

Figure 1:
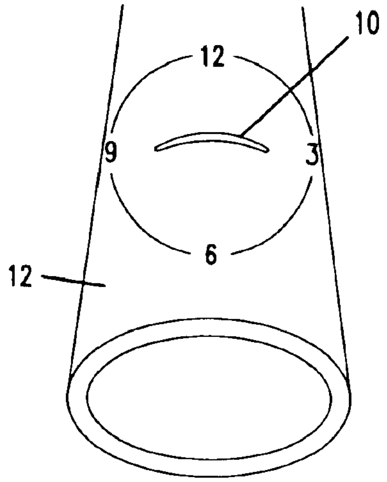
FIG. 1 illustrates an incision into a vessel made with a standard needle (labeled "Prior Art")

While the invention is amenable to various modifications in alternative forms, the specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION OF THE PREFERRED EMBODIMENT

One embodiment of the invention is a hollow cylindrical needle with a bevel face defining a first cutting surface formed in a top surface of one end of the needle. At least one projection is attached to and extends away from the needle near the bevel face. The projection defines at least a second cutting surface. The projection may be a blade that extends perpendicularly away from the needle. In a preferred embodiment, the blade is located behind the bevel face, on the top surface of the needle. In another embodiment, the blade is positioned on the bottom of the needle adjacent the needle tip.

The forward edge of the blade preferably meets the surface of the needle at a right angle or at an acute angle. In alternative embodiments, the blade is a triangle, a trapezoid, a rectangle, a semicircle, or combinations of different shapes.

In a further embodiment, the needle has a second projection defining at least a third cutting surface. The second projection may be positioned near the needle tip and is preferably spaced apart from the first projection.

Another embodiment of the needle involves a projection with first, second, and third free edges. The first free edge may be a semicircle, the second free edge joins the first free edge at an acute angle, and the third free edge joins the second free edge at an obtuse angle. The first free edge may extend into the bevel face of the needle.

A still further embodiment of the invention is a needle with a slot cut in the top surface of the needle adjacent the bevel face and at least one projection positioned such that it is moveable from a first position inside the needle, beneath the slot, to a second position wherein the projection extends through the slot and away from the needle. The projection defines a second cutting surface.

Another embodiment of the invention is a needle with a lumen extending from one end to the other end of the needle, and having a bevel face defining an opening into the lumen with at least one blade positioned substantially perpendicular in the opening and extending above the bevel face.

The invention additionally involves a catheterization assembly made up of a needle with a secondary cutting surface, a guidewire, and a catheter, and methods of using the needle and catheterization assembly.

Another embodiment of the invention is a catheterization assembly involving two needles, a first conventional hollow catheterization needle, and a second, tubular needle with a sharpened projection attached to and extending away from the tubular needle. A method of performing a catheterization using the double needle set involves inserting the first needle into a vessel to make a first cut, passing a guidewire through the first needle into the vessel, withdrawing the first needle, inserting the second needle over the guidewire into the vessel so that the sharpened projection on the second needle makes a second cut that intersects the first cut, withdrawing the second needle, passing a catheter over the guidewire and into the vessel through the opening made by the first and second cuts, and removing the guidewire.

Another embodiment of the invention is a needle assembly that includes a hollow cylindrical needle and a removable cutting member. The removable cutting member includes an elongate portion and a cutting edge secured to one end of the elongate portion. The removable member is capable of being positioned within the needle so that the cutting edge is aligned at an angle relative to a bevel face of the needle to make an incision at an angle relative to a lateral incision made by the bevel face.

Another embodiment of the invention is a removable cutting member that is insertable into a hollow needle. The cutting member includes an elongate shaft having an end to which a cutting edge is secured. The cutting member is capable of being inserted into a hollow needle in a position adjacent a bevel face of the needle so that the cutting edge is aligned at an angle relative to the bevel face.

As used herein, "bevel face" refers to an angled face created by cutting or grinding the top end portion of a hollow cylindrical member. The bevel face comprises at least one cutting surface, a leading portion, and a trailing portion. The cutting surface extends from the leading portion to the trailing portion. The leading portion may be sharpened to form a sharp tip. The sharp tip serves to puncture another member such as a vessel wall or other tissue, and the cutting surface of the bevel face cuts a substantially straight-line incision.

Figure 3:
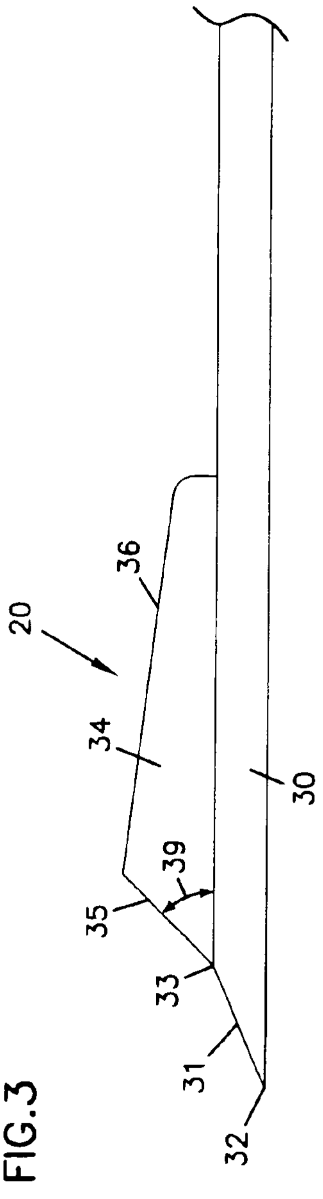
FIG. 3 is a side view of a needle with a projection according the invention.

One embodiment of a needle of the present invention is shown in FIG. 3. The needle 20 comprises a hollow cylindrical member 30 made of any suitable material, including stainless steel. The needle has a bore running through its entire length along a longitudinal axis of the needle to facilitate administration and withdrawal of, for example, fluids or elongate members through the needle. The cylindrical member 30 may be of any suitable diameter, such as a thin wall member having a diameter of 1 to 2 mm (about 18 to 21 gauge) for intravenous injection, to several centimeters in diameter for trocar or other surgical uses.

At the first end, a bevel face 31 is cut into the top surface of the cylindrical member 30. The cut is made at an angle oblique to the longitudinal axis of the cylindrical member. The bevel face 31 defines a first cutting surface extending from a leading portion 32 to a trailing portion 33 of the bevel face. The leading portion 32 may be sharpened to provide a puncturing tip. A projection 34 is attached to and extends away from the cylindrical member. The forward edge 35 of the projection 34 defines a second cutting surface.

In the embodiment illustrated in FIG. 3, the projection is a blade attached to the top surface of the cylindrical member 30, extending from the trailing portion 33 of the bevel face away from the sharp tip of the needle. The blade is positioned adjacent the bevel face to create a second incision which intersects the incision made by the bevel face cutting surface.

The blade may be of any suitable height, length and shape for creating a secondary incision adjacent the primary incision made by the bevel face. The forward edge 35 may extend perpendicularly from the top surface of the cylindrical member 30, as shown in FIG. 10, or the forward edge 35 may be angled at an angle 39 as shown in FIG. 3. The blade may be a triangle, rectangle, trapezoid, octagon, pentagon, semicircle, or any other shape with at least a forward edge that is sharpened. The corners may be sharp angles or may be rounded. The top or rear edges of the blade, if present, may be dull. The blade may be less than 1 mm in length, it may extend the entire length of the cylindrical member, or it may be any length L in between (See FIGS. 4–6 and 9 for various length L). A blade of extended length may provide additional rigidity and maintain the blade in position during insertion and withdrawal of the needle.

In a preferred embodiment of the present invention, the blade has a length that ranges from about 3 to 17.25 mm and more preferably ranges from about 3 to 5 mm. The blade preferably has a height of about 0.5 to 3.25 mm and more preferably has a height of about 0.5 to 1.5 mm.

Figure 4:
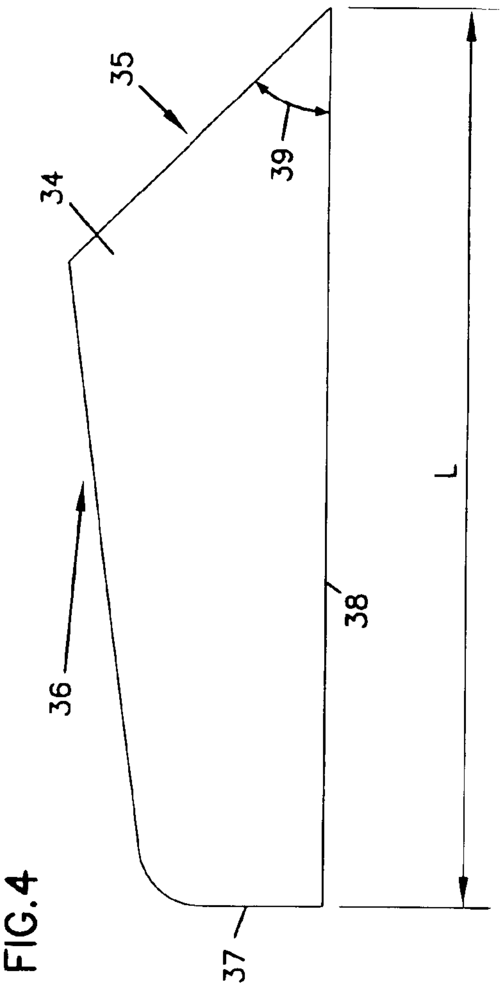
FIG. 4 is a side view of the projection shown in FIG. 3.

FIG. 4 shows an embodiment of a projection 34 with an angled forward edge 35, and upper 36 and rear 37 edges. The upper 36 and rear 37 edges may be dull. In one embodiment, the bottom edge 38 of the projection is 0.45 cm long, and an angle 39 between the bottom edge 38 and the cutting surface is about 45 degrees. The angle between the bottom edge 38 and the forward edge 35 is preferably less than 90 degrees and more preferably is about 25 to 50 degrees. The height of the projection may be from about 0.5 mm to about 5 mm, more preferably about 1 mm for catheterization uses. As stated above, the needle of the invention may be used for other medical procedures, and would be sized accordingly. For example, when used as a trocar, the cylindrical member and projection would be much larger than when used for catheterization. The projection 34 also has a length L from the forward edge 35 to the rear edge 37.

Figure 5:
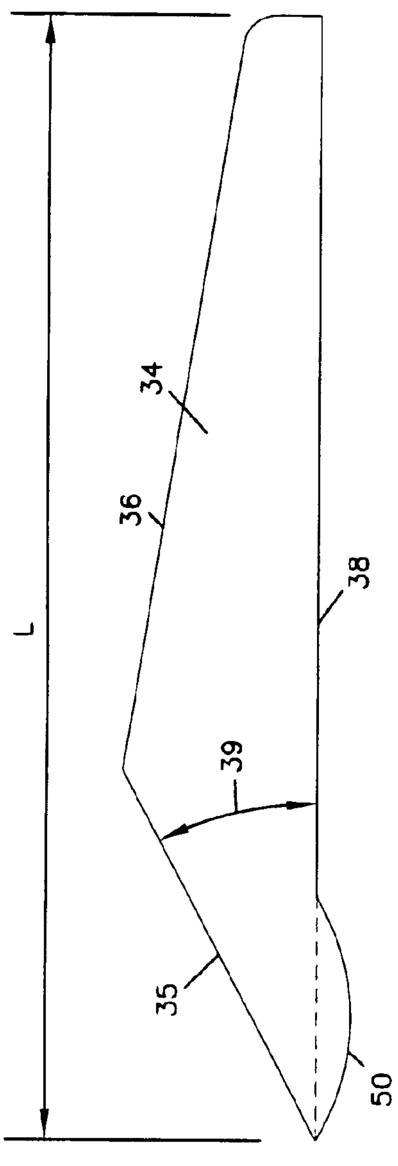
FIG. 5 is a side view of an alternate embodiment of a projection according to the invention.
Figure 6:
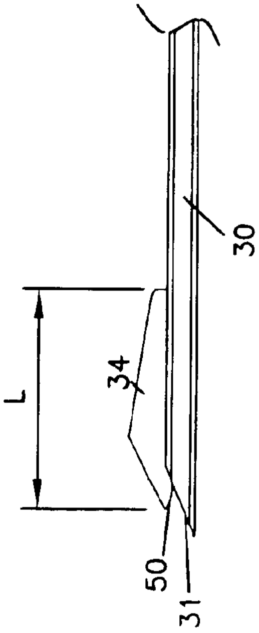
FIG. 6 is a side view of the projection of FIG. 5 in place on a needle.

Another embodiment of the projection 34, illustrated in FIG. 5, has an arc extension 50 on the bottom edge 38 near the junction with the angled forward edge 35. The arc extends below the bottom edge 38. The radius of the arc may, for example, be 0.72 mm, and the angle between the bottom edge 38 and the angle 39 between forward edge 35 and bottom edge 38 may be, for example, about 28 degrees. In the embodiment shown, the projection has a length of about ⅜ inch (9.5 mm). FIG. 6 shows the projection 34 of FIG. 5 in place on a cylindrical member 30, with the arc extension 50 protruding into the hollow cylindrical member 30 at the bevel face 31. The cylindrical member 30, shown in FIG. 6, has an outer diameter of about 0.05 inches (1.27 mm).

Figure 2:
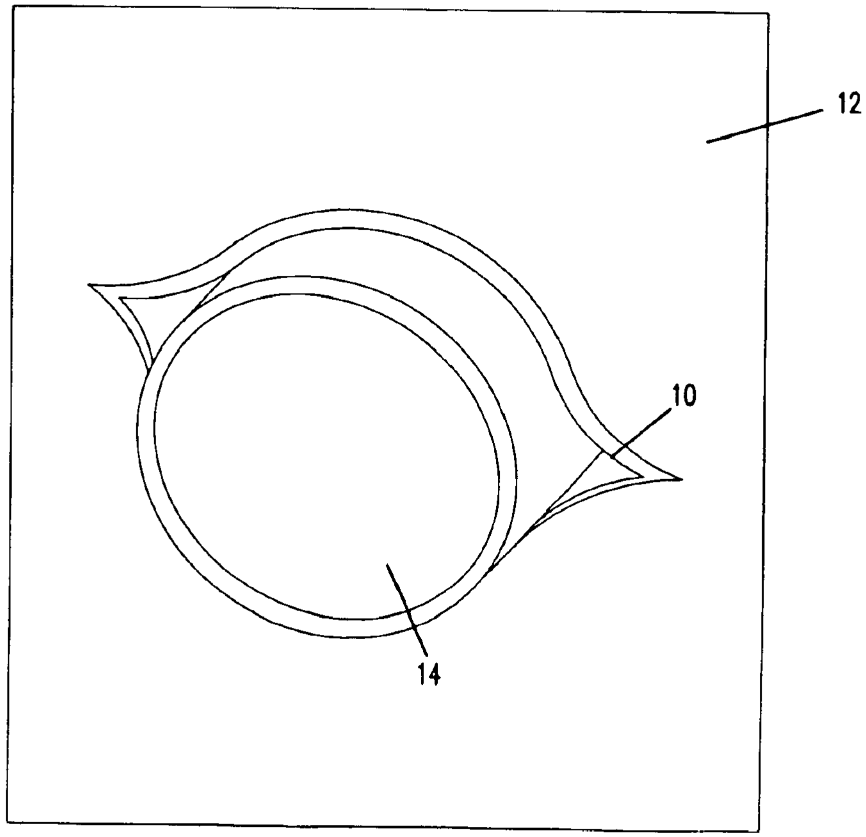
FIG. 2 illustrates a catheter inserted through the incision of FIG. 1 (labeled "Prior Art")
Figure 7:
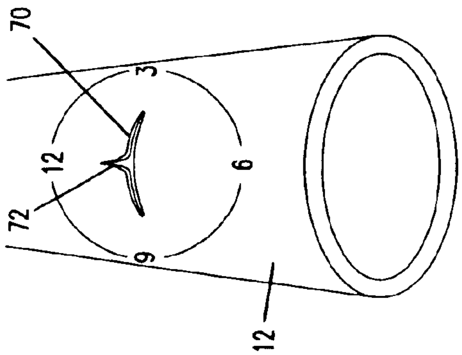
FIG. 7 illustrates an incision into a vessel made with one embodiment of a needle according to the invention.

As stated above, FIG. 1 depicts an incision made by a prior art device and FIG. 2 depicts a hollow tube inserted in such an incision. FIG. 7 illustrates the incisions 70, 72 made using one embodiment of a needle of the present invention. Using the numbers on a clock face for reference, the primary incision 70 made by the bevel face cutting surface is between the 3 and 9 o'clock positions, and the secondary incision 72 made by the projection extends perpendicularly from the primary incision 70. In this embodiment, the incisions are in a "T" configuration. The projection, and necessarily the secondary incision, may be positioned at any location around the cylindrical member.

Additionally, multiple projections may be positioned around the cylindrical member. In one embodiment, two projections, one at 12 o'clock and one at 6 o'clock, are attached to the cylindrical member to achieve a "+" incision pattern.

The "T" or "+" incision patterns allow for using a smaller needle that is closer in diameter to the catheter to be inserted, and creates a better seal around the catheter. Using a standard needle, making a straight-line incision, the width of the incision must be at least half the circumference of the catheter to be inserted:

$$w = \pi \cdot \frac{d}{2}$$

where w is the incision width and d is the diameter of the catheter to be inserted.

An incision pattern involving two or more incisions allows for a reduction in overall incision width by up to 50%, with w=d. Additionally, the use of a multi-incision pattern reduces the likelihood of a tear in the vessel wall upon removal of the catheter sheath.

Figure 9:
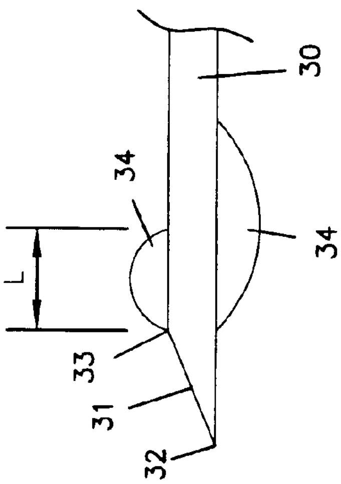
FIG. 9 is side view of an alternate embodiment of a needle according to the invention.
Figure 8:
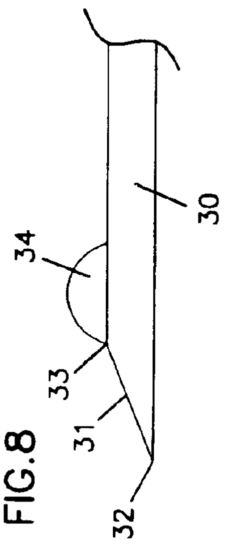
FIG. 8 is a side view of an alternate embodiment of a needle according to the invention.
Figure 10:
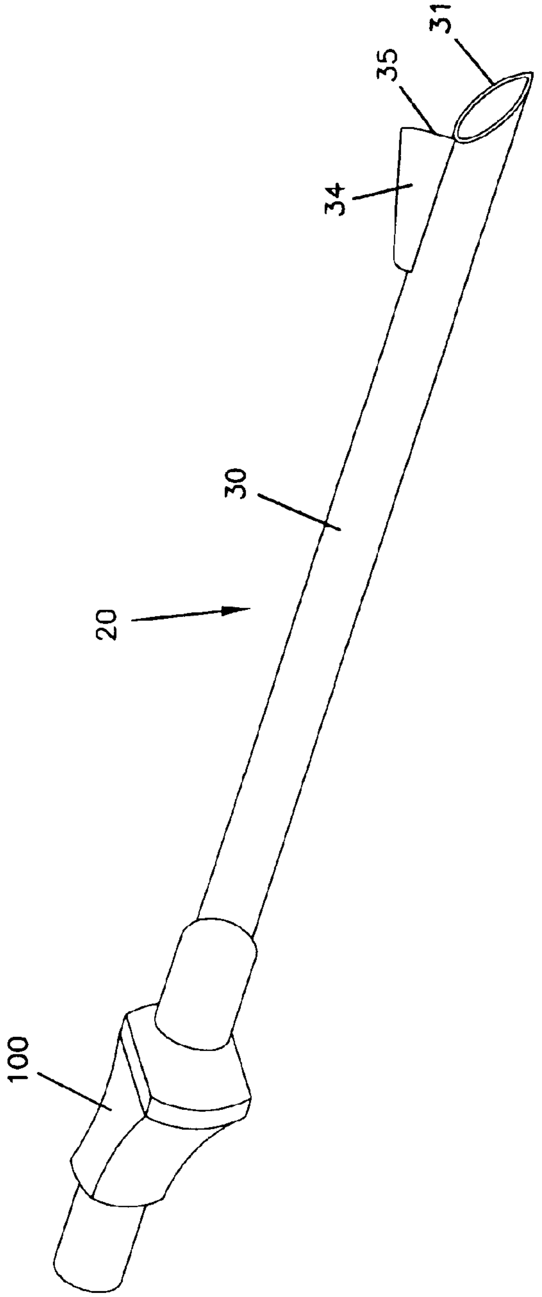
FIG. 10 is a perspective view of a needle of the invention attached to a hub assembly.

FIGS. 8 and 9 illustrate embodiments involving semicircular projections. The projections may be any shape with a forward cutting surface.

FIG. 10 shows a needle 20 of the invention attached to a hub assembly 100. The hub assembly may be helpful when handling and positioning the needle. The hub assembly may also be useful in a catheterization or other procedure involving needle 20 when additional devices must be inserted into or positioned relative to the needle. Projection 34, in this embodiment, has a forward edge 35 that is substantially perpendicular to the outer surface of cylindrical member 30.

Figure 11:
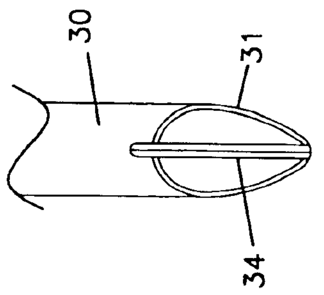
FIG. 11 is a top view of an alternate embodiment of a projection in place on a needle according to the invention.

Another embodiment of the needle of the invention, shown in FIG. 11, has a projection 34 positioned within the hollow cylindrical member 30 at the bevel face 31. The projection is a blade that bisects the bevel face 31. The blade may extend from the sharpened tip to the trailing portion of the bevel face, or it may be positioned anywhere in between. The blade extends above the level of the bevel face. The height of the blade above the bevel face may be less than 1 mm, more than 1 mm, or even more than 1 cm, depending on the size of the needle and the size of the incision to be made.

Figure 12:
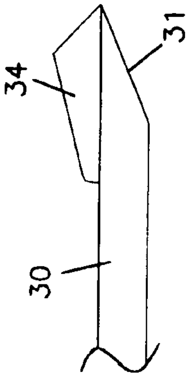
FIG. 12 is a side view of an alternate embodiment of a projection in place on a needle according to the invention.

FIG. 12 illustrates an embodiment in which the projection 34 is positioned on the bottom surface 150 of the cylindrical member 30. In this embodiment, the needle may be inserted into the vessel either bevel-up or bevel-down. The projection may also be positioned at any other location around the cylindrical member. When multiple projections are present, they may be positioned opposite each other, adjacent each other, or at any location around the cylindrical member.

Figure 13:
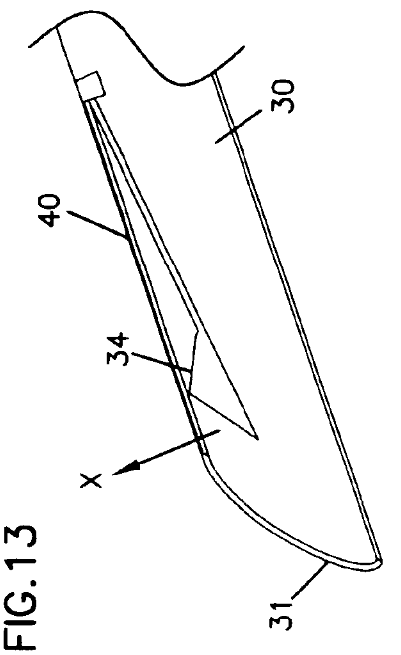
FIG. 13 is a cross-sectional side view of an embodiment of a moveable projection in the recessed position according to the invention.
Figure 14:
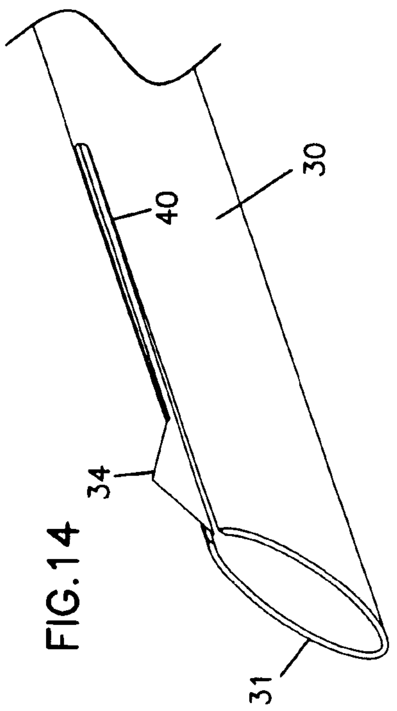
FIG. 14 is a side view of the embodiment of FIG. 16 with the projection in the extended position.

FIGS. 13 and 14 illustrate an embodiment of the invention in which the projection 34 is moveable from a first position inside the cylindrical member 30 (FIG. 13) to a second position outside the cylindrical member 30 (FIG. 14). The cylindrical member 30 has an opening, such as a slit 40, in the top edge of the needle adjacent the trailing portion of the bevel face. The opening is sized to accommodate the projection. The means for moving the projection may be a spring, a lever, release wire, or any other mechanism that achieves the desired movement. In use, the needle is inserted into the vessel with the projection in the first position, creating the primary incision. The projection is then moved to the second position and the needle is withdrawn. The secondary incision is created as the needle is withdrawn. In other embodiments, the projection may be in the first position when the needle in directed to the insertion site, and then moved into the second position prior to inserting the needle into the vessel.

In yet another embodiments using the configuration of FIGS. 13 and 14, the projection may be in the first position when inserted in the vessel, and then moved into the second position prior to removal of the needle from the vessel. This embodiment may be useful for projections of different shapes that may be difficult to remove from the vessel otherwise.

Figure 15B:
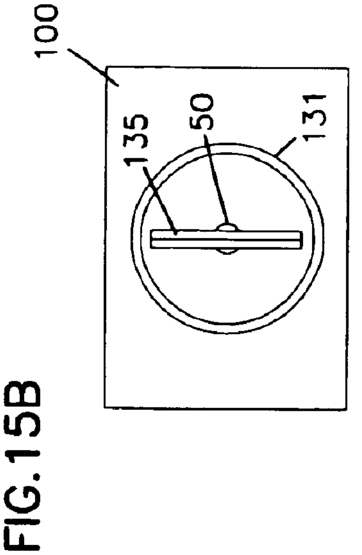
FIG. 15B is an end view of the embodiment of FIG. 15A.
Figure 15A:
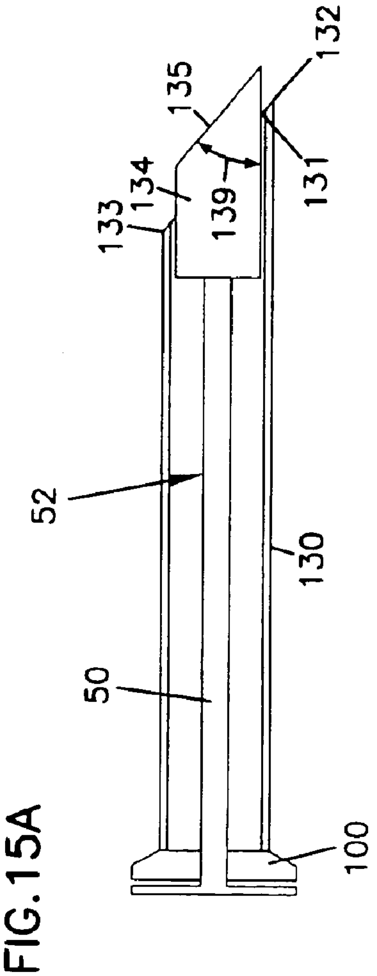
FIGS. 15A is a cross-sectional side view of an alternative embodiment according to the invention.

FIGS. 15A and 15B illustrate an embodiment of the invention in which the projection is part of a stylet 52 that is removable from the needle. The stylet is preferably inserted into the needle prior to the needle being inserted into a vessel. However, the stylet may be inserted into the needle after the needle has been inserted into the vessel. In some embodiments, the stylet is permanently fixed to the needle in a given position relative to the bevel face of the needle. In other embodiments, the stylet position is adjustable to adjust a radial and longitudinal position of the stylet relative to the needle. For example, the stylet may be adjusted longitudinally so that it engages the vessel prior to or after the bevel face of the needle engages the vessel. The stylet position may be controlled or held in a given position via a hub assembly 100 secured to an end of a needle 130.

The stylet 52 includes an elongate shaft 50 and a projection 134 secured to the shaft. The projection may be shaped as a triangle, rectangle, trapezoid, octagon, pentagon, semicircle, or any other shape with at least a forward or cutting edge 135 that is sharpened. The corners of the projection may be sharp angles or may be rounded. The top or rear edges of the blade, if present, may be dull. The blade may be less than 1 mm in length, it may extend the entire length of the stylet, or it may be any length there between.

The projection 134 is positioned within the hollow needle at an angle relative to bevel face 131 of the needle. In a preferred arrangement, projection 134 is in the 12 o'clock position so that it forms a vertical cut that intersects and is substantially perpendicular to a lateral insertion made by the bevel face of the needle. In other arrangements, projection 134 is positioned at angles greater or less than 90 degrees. In yet other arrangements, projection 134 may include multiple cutting edges positioned at multiple angles relative to bevel face 131 of the needle that form multiple insertions in a vessel, all of which intersect the lateral insertion made by the bevel face.

Figure 16B:
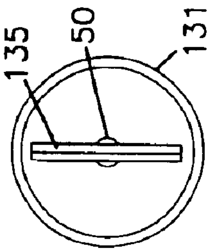
FIG. 16B is an end view of the embodiment of FIG. 16A.
Figure 16A:
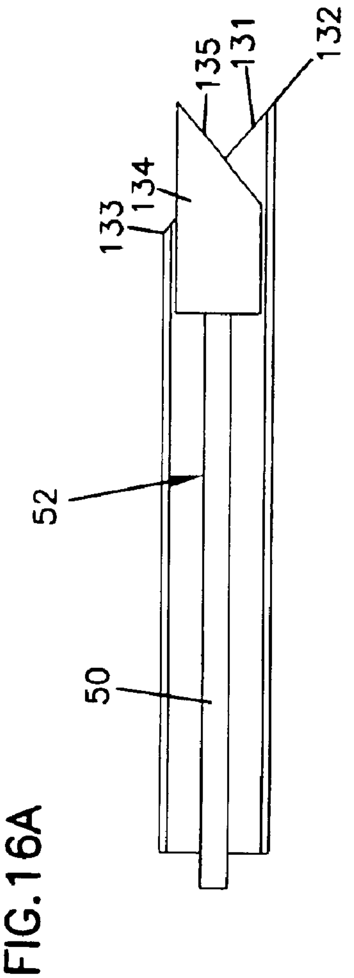
FIG. 16A is a cross-sectional view of an alternative embodiment according to the invention.

The projection 134 of FIG. 15A includes a forward or cutting edge 135 having an angle 139 that is angled in a similar direction to the bevel of bevel face 131. Angle 139 may be less than 90 degrees and is preferably 20–50 degrees. FIGS. 16A and 16B illustrate cutting edge 135 angled in the opposite direction (180 degrees opposite) to bevel face 131. According to the arrangement of FIGS. 16A and 16B, the cutting edge 135 forms an insertion into a vessel that does not immediately intersect the lateral insertion created by bevel face 131.

According to a method of inserting a needle and a catheter using the stylet of FIGS. 15A, 15B, 16A and 16B, the stylet is inserted into a hollow needle, the needle is inserted into a vessel creating a lateral insertion and an intersecting angled insertion, the stylet is removed from the needle, a guidewire is inserted through the needle into the vessel, the needle is removed, and a catheter is inserted or the guidewire into the vessel. The steps of this method do not necessarily need to be practiced in the order listed above, and may include more or fewer steps to accomplish the same or similar results.

It is appreciated that the projection 134 of FIGS. 15A, 15B, 16A and 16B may include the same or similar features as those illustrated and described above relating to FIGS. 3–14, so long as those features are adaptable to a stylet that is insertable into a hollow needle.

The above specification, examples and data provide a complete description of the manufacture and use of the composition of the invention. Since many embodiments of the invention may be made without departing from the spirit and scope of the invention, the invention resides in the claims hereinafter appended.

I claim:

1. A needle assembly comprising:

a first needle portion comprising a hollow cylindrical member having a longitudinal axis and first and second ends, and a bevel face defined by the first end, the first needle portion being configured to make a first linear incision; and a second needle portion comprising an elongate member having a longitudinal axis and first and second ends, and a cutting edge secured to the first end of the elongate member, the second needle portion being insertable into the first needle portion to position the cutting edge adjacent to the first end of the first needle portion, the second needle portion being configured to make a second linear incision that is not aligned with the first linear incision.

2. The needle assembly of claim 1 wherein the first and second linear incisions are aligned substantially perpendicularly to each other.

3. The needle assembly of claim 1 wherein the second end of each of the first and second needle portions comprise a hub portion, wherein the hub portions fix the position of the cutting edge relative to the bevel face.

4. The needle assembly of claim 1 wherein the cutting edge is a bevel blade.

5. A needle assembly comprising:

a first needle portion comprising a hollow cylindrical member having a longitudinal axis and first and second ends, and a bevel face formed in the first end, the bevel face being configured to make a first incision; and a second needle portion comprising an elongate member baying a longitudinal axis and first and second ends, and a cutting edge coupled to the first end of the elongate member, the second needle portion being insertable into the first needle portion to position the cutting edge relative to the bevel face, the cutting edge being configured to make a second incision that intersects the first incision at an angle relative to the first incision.

6. The needle assembly of claim 5 wherein the cutting edge is configured to make the second incision at a plurality of angles relative to the first incision.

7. The needle assembly of claim 5 wherein the second end of each of the first and second needle portions comprise a hub portion, wherein the hub portions fix the position of the cutting edge relative to the bevel face.

8. The needle assembly of claim 5 wherein the cutting edge is a bevel blade.

* * * * *